United States Patent
Shenfarber

(10) Patent No.: US 11,877,642 B1
(45) Date of Patent: Jan. 23, 2024

(54) HANDLE DEVICE FOR PROVIDING OXYGEN AT THE HEAD OF A SKIN CARE DEVICE

(71) Applicant: OMM Imports, LLC., Doral, FL (US)

(72) Inventor: Moti Shenfarber, Doral, FL (US)

(73) Assignee: OMM Imports LLC, Doral, FL (US)

( * ) Notice: Subject to any disclaimer, the term of this patent is extended or adjusted under 35 U.S.C. 154(b) by 0 days.

(21) Appl. No.: 18/121,515

(22) Filed: Mar. 14, 2023

Related U.S. Application Data

(63) Continuation-in-part of application No. 29/852,960, filed on Sep. 12, 2022.

(51) Int. Cl.
*A61M 35/00* (2006.01)
*A45D 44/00* (2006.01)
*A61N 5/06* (2006.01)

(52) U.S. Cl.
CPC ............. *A45D 44/00* (2013.01); *A61M 35/30* (2019.05); *A61N 5/0616* (2013.01)

(58) Field of Classification Search
CPC ................. A61M 35/30; A61N 5/0616; A45D 2200/205; A45D 2200/057
See application file for complete search history.

(56) References Cited

U.S. PATENT DOCUMENTS

| | | | |
|---|---|---|---|
| 7,384,405 B2 * | 6/2008 | Rhoades | A61H 7/005 601/138 |
| 10,507,140 B2 | 12/2019 | Quisenberry | |
| 2001/0032000 A1 | 10/2001 | Dotan | |
| 2006/0058714 A1 | 3/2006 | Rhoades | |

FOREIGN PATENT DOCUMENTS

| | | |
|---|---|---|
| KR | 20090123119 A | 12/2009 |
| KR | 20130139526 A | 12/2013 |
| KR | 20140025906 A | 3/2014 |
| KR | 101497620 B1 | 3/2015 |
| KR | 101590170 B1 | 2/2016 |
| KR | 20170042173 A | 4/2017 |
| KR | 102091241 B1 | 3/2020 |
| KR | 20210009474 A | 1/2021 |
| WO | 2013081211 | 6/2013 |
| WO | 2021025315 | 2/2021 |
| WO | 2021034046 | 2/2021 |
| WO | 2022085526 | 4/2022 |

\* cited by examiner

*Primary Examiner* — Deanna K Hall
(74) *Attorney, Agent, or Firm* — The Concept Law Group, PA; Scott D. Smiley; Scott M. Garrett

(57) ABSTRACT

A handle device for use with a hand held portable skin care device has a gas emitting portion that is configured to be proximate to the head of the skin care device during use with the skin care device. The gas emitting portion of the handle device has one or more gas openings. The handle device also includes an inlet that is fluidly coupled to the one of more gas openings through a channel in the handle device. During use, oxygen can be provided to the inlet, and emitted through the one or more gas openings as the skin care device is used to provide therapeutic light to the user's skin.

20 Claims, 12 Drawing Sheets

HANDLE DEVICE FOR PROVIDING OXYGEN AT THE HEAD OF A SKIN CARE DEVICE

CROSS-REFERENCE TO RELATED APPLICATION

This application is a continuation in part of U.S. design application Ser. No. 29/852,960, filed Sep. 12, 2022, the entirety of which is hereby incorporated by reference.

FIELD OF THE INVENTION

The present invention relates generally to portable handheld skin care devices, and, more particularly, relates to a device, system, and method for administering light and oxygen therapy to a user's skin, particularly on the face.

BACKGROUND OF THE INVENTION

It has long been known that the application of certain wavelengths of light to human skin can be beneficial in keeping the skin healthy, and reducing the effects of aging. Accordingly, there have been a wide variety of skin care devices that emit those wavelengths of light through a transparent or translucent head that is held near, if not against the user's skin. These devices have become very popular for treating and maintaining skin in good health, and reducing the effects of aging, exposure to pollutants, and other factors that can prematurely age the skin. In order to provide additional benefits, manufacturers have added heat elements, vibration, and additional wavelengths of light to these devices.

A typical home skin care device is portable and hand held, having a body that houses one or more battery cells that can be rechargeable, as well as the electronics and circuitry to generate and control light output by the device, and also heat and vibration if included in the design. The light is emitted at a transparent head that is positioned near, or against the user's skin, such as on the face. The user then slowly moves the device around to expose portions of the skin to the light, heat, and/or vibration. A common design of such devices is a generally cylindrical or slightly conical body having a base and a head. The head has a flat surface defining a plane that can angled at, for example, about forty five degrees (+/−ten degrees) relative to an axis of the body to allow the user to hold the device at an angle when applying the head to the user's face. In order to be portable, it is a design goal of these devices to be lightweight so that they do not cause undue fatigue during use.

In addition to light, heat, and vibration, it is further believed that applying oxygen to the skin can greatly aid in keeping the skin healthy. Accordingly, devices for generating oxygen and applying the generated oxygen to a user's skin have been developed. However, an oxygen generator is not, generally, a handheld device. Instead, a tube runs from the oxygen generator to an applicator that emits the oxygen. However this means that the oxygen applicator must be used alternatively with the hand-held light applicator. Or, if the oxygen applicator is designed to include light elements, then the user is duplicating the functionality if they already have a portable skin care device, which is an unnecessary expense.

Therefore, a need exists to overcome the problems with the prior art as discussed above.

SUMMARY OF THE INVENTION

In accordance with some embodiments of the inventive disclosure, there is provided a handle device for emitting a gas proximate to a head of a skin care device that includes a halo that at least partially surrounds the head of the skin care device. The halo has an internal channel, and a plurality of gas openings that are fluidly coupled to the channel. The handle device further has an inlet that has a bore that is fluidly coupled to the internal channel of the halo.

In accordance with a further feature, the halo has a front surface in which the plurality of gas openings are disposed, and which faces in a same direction as the head of the skin care device.

In accordance with a further feature, the handle device further includes a stem having a top, and wherein the halo is coupled to the top of the stem.

In accordance with a further feature, the halo is hingeably coupled to the top of the stem, and is moveable between a raised and a lowered position.

In accordance with a further feature, the inlet is disposed on the stem, and the stem includes a channel from the inlet to the internal channel of the halo.

In accordance with a further feature, the stem extends to a base that is configured to bear against a portion of the skin care device.

In accordance with a further feature, the inlet is disposed on the base, and is fluidly coupled to a channel in the stem that is coupled to the internal channel in the halo.

In accordance with a further feature, the stem has a bottom and the device further includes a pair of opposing clip members configured to extend partly around a body of the skin care device.

In accordance with some embodiments of the inventive disclosure, there is provided a handle device for use with a skin care device, where the skin care device has a body with a head at one end of the body and a bottom at an opposite end of the body from the head. The handle device includes a base that has a top or top surface that is configured to bear against the bottom of the skin care device. The handle device also has a stem that extends from the base to a top of the stem. The handle device further includes a halo coupled to the top of the stem by a hinge such that the halo is moveable about the hinge between a lowered position and a raised position. The halo is configured to substantially surround the head of the skin care device and has a through opening configured to allow the head of the skin care device to extend through the halo. The halo further has a top surface that has a plurality of gas openings around the top surface of the halo, and the halo further has a channel inside the halo that is fluidly coupled to each gas opening of the plurality of gas openings. The handle device also has an inlet that has an opening, wherein there is a channel inside the handle device between the opening of the inlet and the channel inside the halo.

In accordance with a further feature, the inlet extends from the base, and the channel extends through the stem to the halo.

In accordance with a further feature, the stem extends from a back of the base, at the top of the base.

In accordance with a further feature, in the lowered position, the top surface of the halo is configured to be set back from a front surface of the head of the skin care device.

In accordance with some embodiments of the inventive disclosure, there is provided a handle device for use with a skin care device. The skin care device has a body with a head at one end of the body and a bottom at an opposite end of the body from the head. The handle device includes a gas emitting portion that is configured to be positioned proximate to the head of the skin care device, and has at least one gas opening. The handle device further includes an inlet, and there is a channel inside the handle device between the inlet and the at least one gas opening of the gas emitting portion.

In accordance with a further feature, the gas emitting portion is a halo that is configured to at least partially surround the head of the skin care device, and the handle device further includes a base, a stem extending from the base where the stem has a top, and wherein the halo is coupled to the top of the stem. The inlet is located on the base the channel extends through the stem to the halo.

In accordance with a further feature, in the halo is couple to the top of the stem at a hinge that allows the halo to be moved between a raised position and a lowered position.

In accordance with a further feature, the handle device further includes a stem having a top, the gas emitting portion is connected to the stem at the top of the stem, and the stem has a bottom from which a pair of opposing clip members extend that are configured to clip onto a body of the skin care device.

In accordance with a further feature, the gas emitting portion is a halo that is circular and is configured to at least partially surround the head of the skin care device.

In accordance with a further feature, the at least one gas opening is a plurality of gas openings distributed around the halo.

Although the invention is illustrated and described herein as embodied in a skin care device holder for use with an oxygen generator, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time.

"In the description of the embodiments of the present invention, unless otherwise specified, azimuth or positional relationships indicated by terms such as "up", "down", "left", "right", "inside", "outside", "front", "back", "head", "tail" and so on, are azimuth or positional relationships based on the drawings, which are only to facilitate description of the embodiments of the present invention and simplify the description, but not to indicate or imply that the devices or components must have a specific azimuth, or be constructed or operated in the specific azimuth, which thus cannot be understood as a limitation to the embodiments of the present invention. Furthermore, terms such as "first", "second", "third" and so on are only used for descriptive purposes, and cannot be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the article being referenced. Those skilled in the art can understand the specific meanings of the above-mentioned terms in the embodiments of the present invention according to the specific circumstances.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

DETAILED DESCRIPTION

Figure 1:
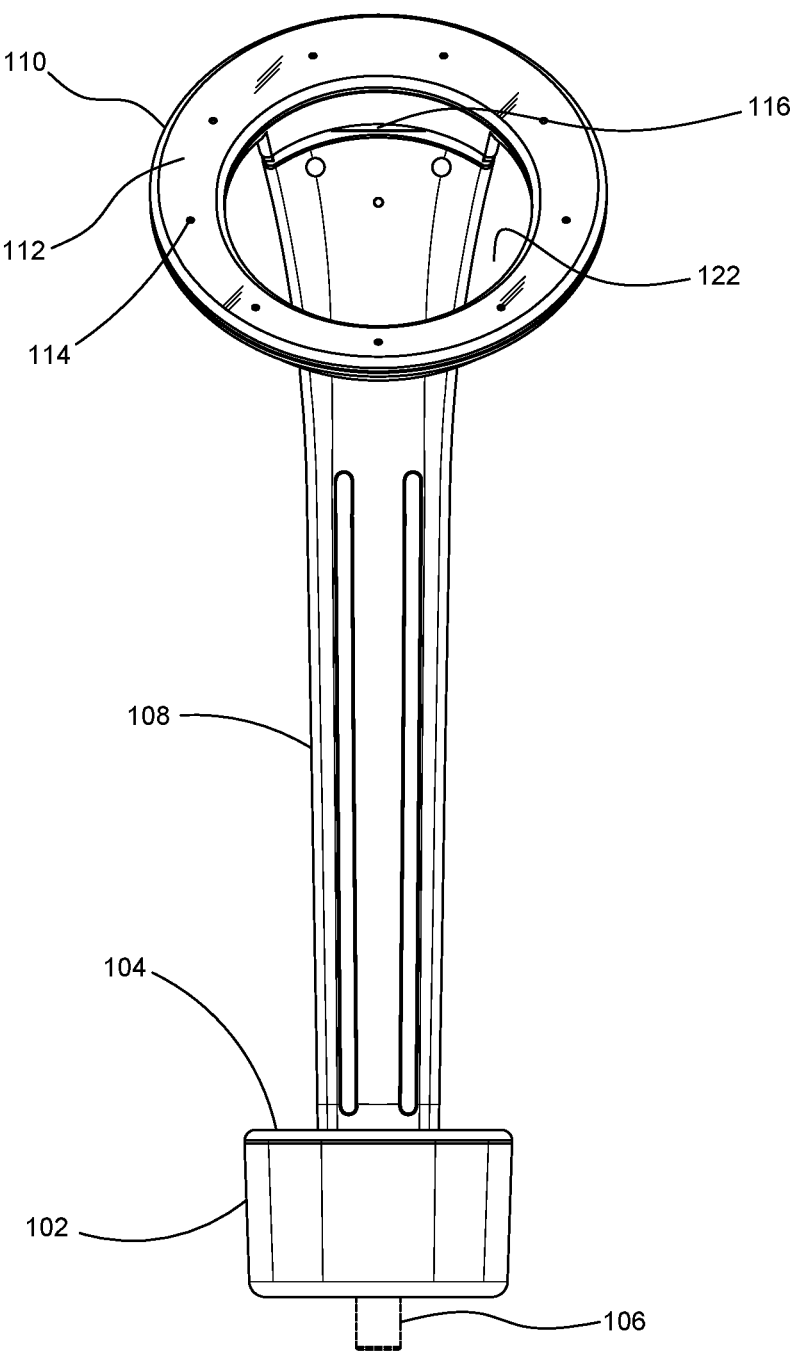
FIG. 1 is a front elevational view of a handle device for use with a skin care device, in accordance with some embodiments.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient combination oxygen applicator and skin care device holder that holds a skin care device. The skin care device emits light, and the handle/holder provides oxygen from an oxygen generator at a location proximate to the head of the skin care device. Although the intended purpose of the device of the present disclosure is to provide oxygen, the inventive device will equally apply other forms of gasses as well, as will be appreciated by those skilled in the art. In general, the device holds, or attaches to a skin care device that is configured to emit light at wavelengths beneficial to the skin, and has a portion that at least partly surrounds the head or light emitting portion of the skin care device so that the oxygen being emitted by the handle device is in close proximity to the head of the skin care device. In some embodiment the handle device includes a gas emitting portion that can be shaped like a halo. The halo-shaped portion can partially encircle the head of the skin care device in a plane that is generally parallel to a plane defined by the head of the skin care device, which is intended to be generally parallel to the skin surface of the user when the skin care device is used. In general, the gas emitting portion is configured to be proximate to the head of the skin care device when the handle device is attached to or holding the skin care device.

FIG. 1 is a front elevational view of a handle device 100, in accordance with some embodiments. The handle device 100 is intended to both hold a conventional skin care device of a certain general form factor, and also emit oxygen generated by an oxygen generator at a location proximate to the head of the skin care device. The skin care device is generally an elongated, generally cylindrical device that has a base at a bottom end and a head at a top end of the skin care device. The head of the skin care device can provide a flat, surface that defines a plane that can be, in some embodiments, at about a forty five degree angle to an axis of the body of the skin care device. Light is emitted at the surface, either directly by light elements through the surface (e.g. openings in the surface) or the surface can be a transparent or translucent cover member through which light is emitted. Other skin care devices can have other configurations. For skin care devices that use a transparent cover member, behind the transparent surface, or directly at the transparent surface, there can be several light emitting elements such as light emitting diodes (LEDs) that are configured to emit particular wavelengths of light. In particular, generally red light in the range of 660-850 nm wavelength, which includes near-infrared light. Other wavelengths may be used in some applications, and in some devices there may be light emitting elements for different wavelengths to combine the effect of multiple wavelengths. For example, in some devices blue light in the range of 415 nm is used. Other skin care devices can have an opaque cover member with openings through which light is emitted by light elements positioned behind the cover that are located in alignment with the openings.

Figure 2A:
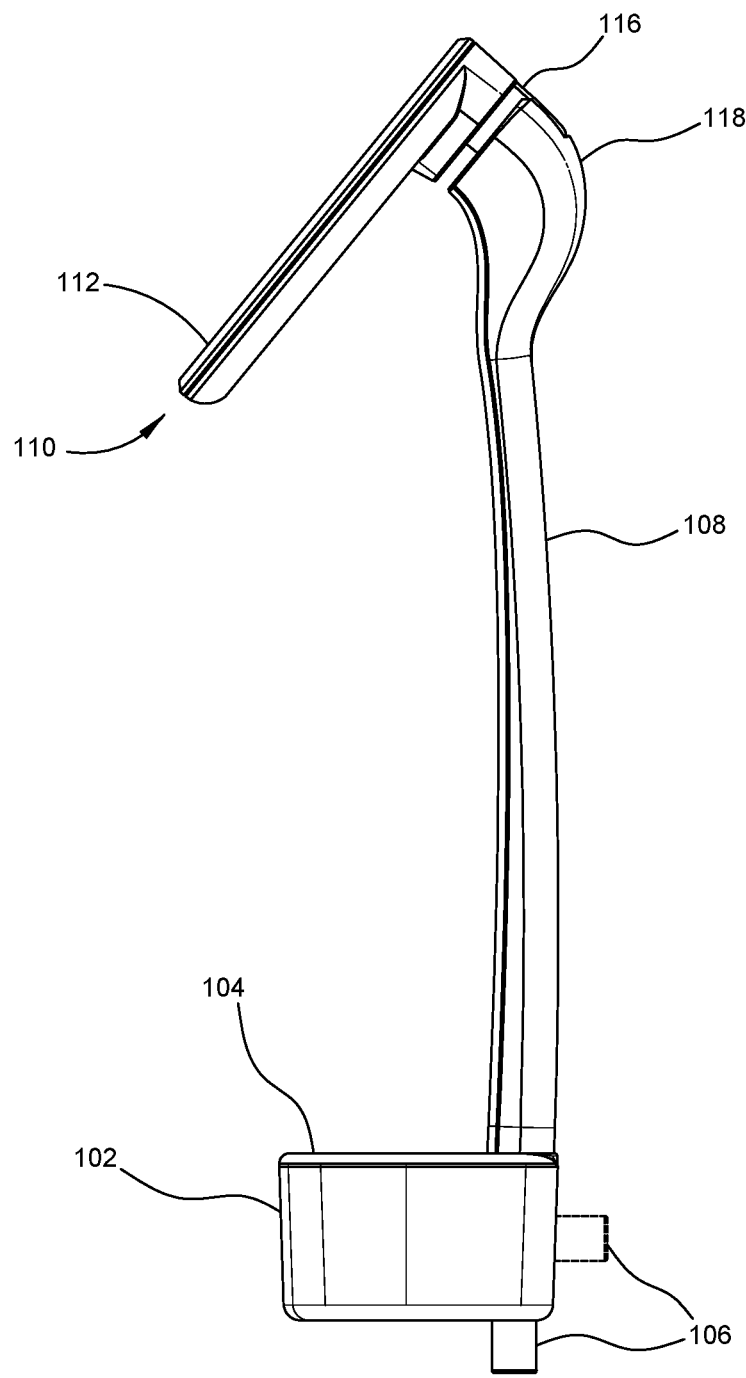
FIG. 2A is a side elevational view of the handle device with the skin care device, with the halo of the handle device in a lowered position, in accordance with some embodiments.
Figure 2B:
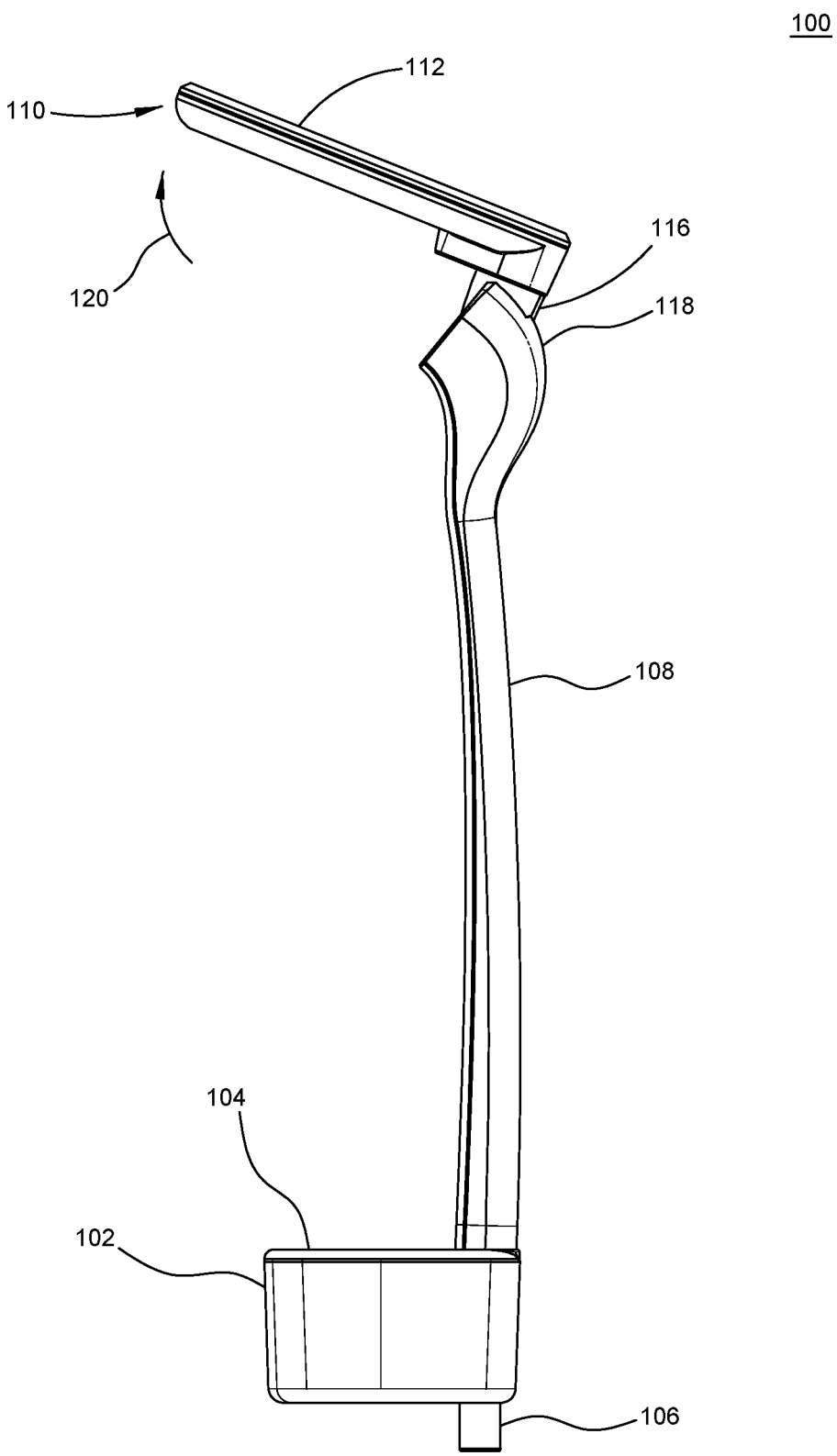
FIG. 2B is a side elevational view of the handle device with the skin care device, with the halo in a raised position, in accordance with some embodiments.

In general, referring to FIGS. 1, 2A, 2B, and 3, the handle device 100 can include a base 102 which has a top surface 104 on which the bottom of the skin care device will rest. An inlet 106 can be provided on the bottom or on the side (e.g. as in FIG. 2A) of the base 102. The inlet 106 is a connector that receives a tube or hose that carries oxygen from an oxygen generator. It will be appreciated by those skilled in the art that, although oxygen is described as an example of a gas that can be emitted by the handle device 100, other gasses, including air, chilled air, heated air, or other gasses, can likewise be emitted from the handle device equivalently. The inlet 106 can be a simple friction fit connector where the exterior diameter of the inlet 106 is sized to be the same or slightly larger than the inner diameter of the tube/hose so that the end of the tube/hose can be pushed over the inlet 106 and retained by friction while also creating a seal around the inlet 106. A stem 108 extends upwards from the base 102 generally at a right angle to the top surface of the base 102. As shown here, the stem can extend from the back of the base 102 so that the bottom of the skin care device can rest on the top surface 104 of the base 102. The inlet 106 has in internal bore that is contiguous with a channel or bore through the base 102 to a similar channel or bore inside the stem 108 to a top 118 of the stem 108 where it meets a hinge 116. The hinge 116 allows a gas emitting portion such as a halo 110 to rotate relative to the stem 108, and has a portion within the top 118 of the stem 108 that is connected to the halo 110. The halo 110 is generally circular having a through opening 122 which is configured and sized to allow the head of the skin care device to pass through the through opening 122. The hinge allows the halo 110 to be lifted to a raised position, as shown in FIG. 2B and indicated by arrow 120, so that the skin care device can be placed in the handle device 100, and then lowered to the lowered position of FIG. 2A. The halo 110 has a top surface 112 that has a plurality of gas openings 114 that fluidly connect to a channel inside the halo 110 which is further fluidly connected through the hinge 116 to the channel in the stem 108. Thus, there is a continuous and contiguous fluid channel from the inlet 106 to the gas openings 114, and oxygen, air, or other gasses that are pumped into the inlet 106 will pass through the internal channel and be emitted through the gas openings 114.

It will be appreciated by those skilled in the art that the gas emitting portion can have other shapes and configurations other than the halo or a partial halo, and achieve an equivalent result. The gas emitting portion is configured to provide a gas opening proximate to the head of the skin care device, so that during use of the skin care device, oxygen will be emitted to the skin of the user in the area of skin being exposed to the light provided by the skin care device.

Figure 2C:
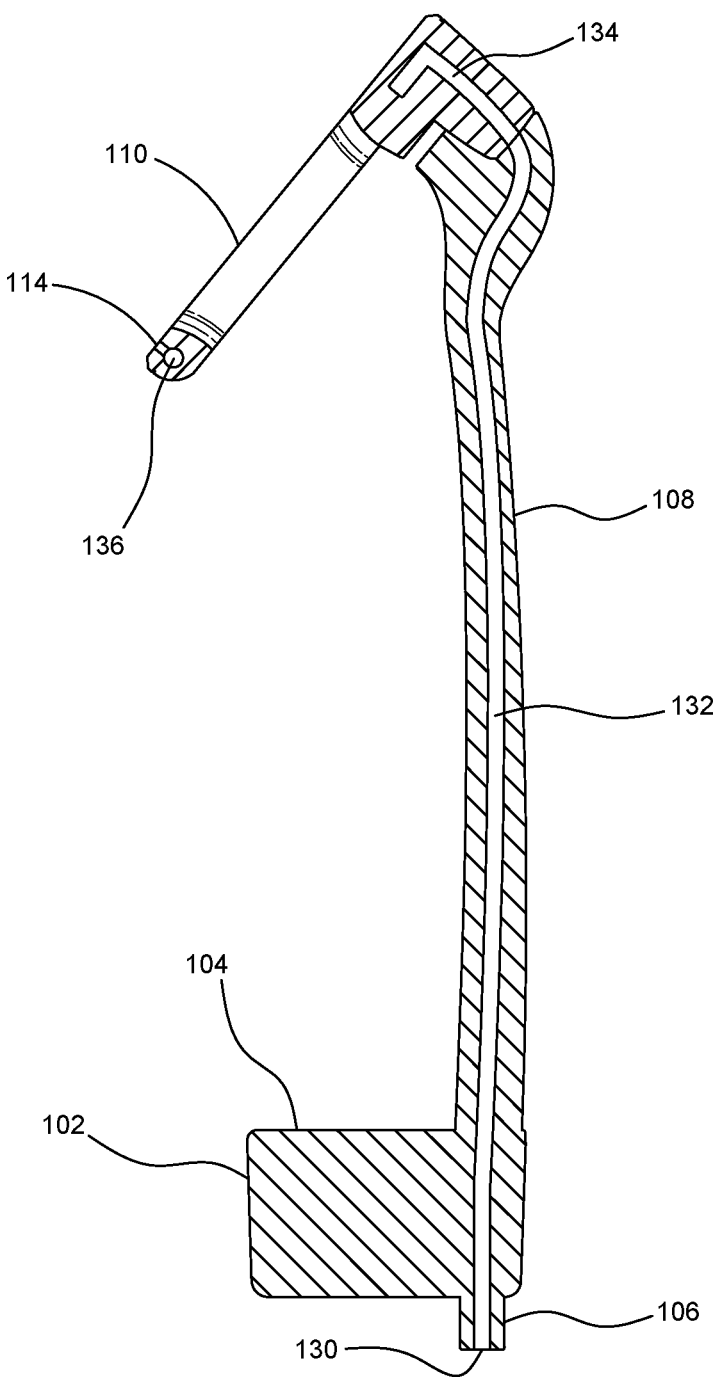
FIG. 2C is a side cut-away view of the handle device with the skin care device, in accordance with some embodiments.
Figure 3:
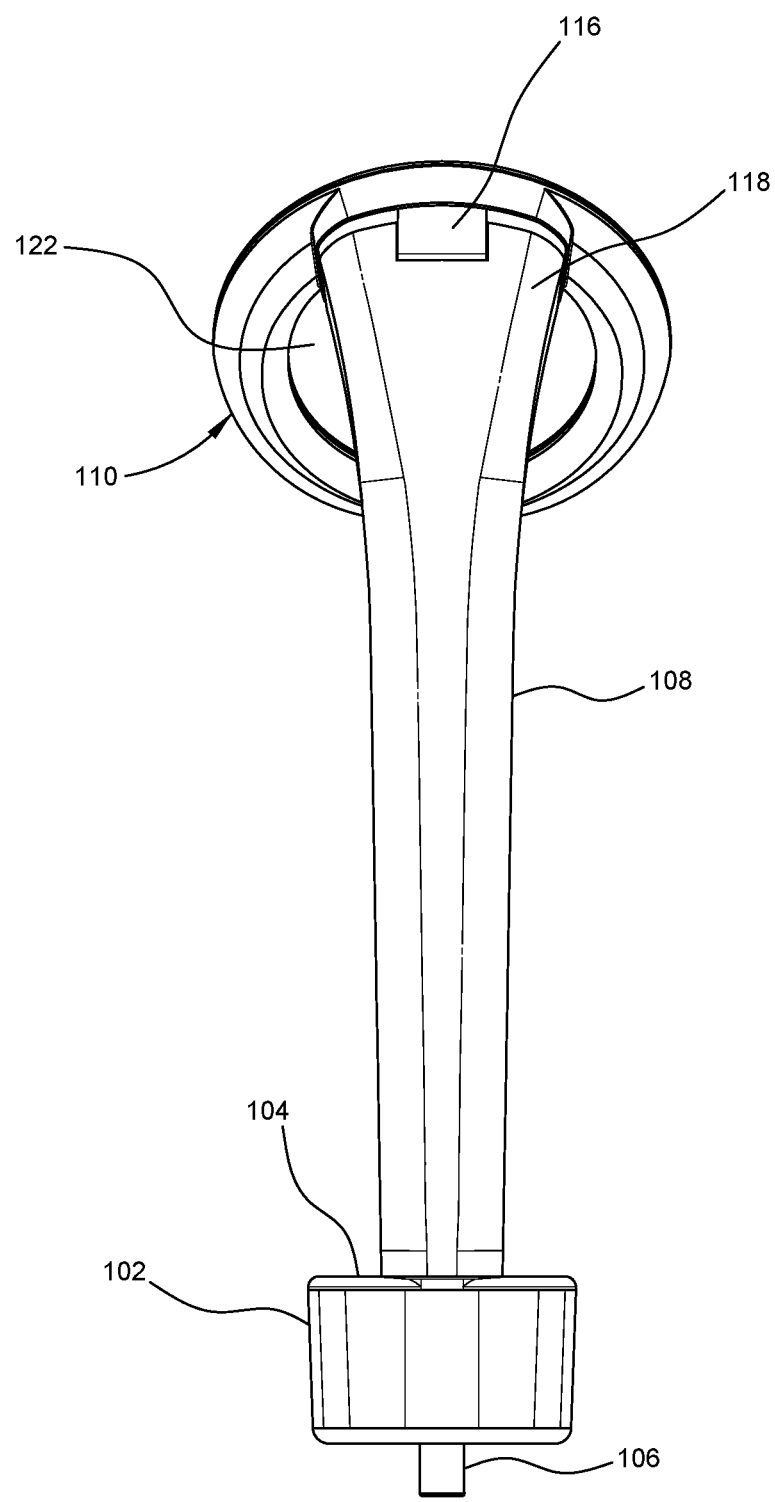
FIG. 3 is a rear elevational view oft the handle device with the skin care device, in accordance with some embodiments.

FIG. 2C shows a cut-away view of the handle device 100 taken centrally in a vertical direction. The inlet 106 includes an opening 130 where oxygen or another gas or gas mixture enters the handle device 100. The opening 130 is the start of contiguous fluid channel through the handle device 100 that includes a base and stem portion 132 of the channel that passes through the base 102 and stem 108 to a halo portion 136 of the channel through a hinge portion 134. The halo portion 136 forms a ring around the inside of the halo 110 and is fluidly connected to gas openings 114. Accordingly, a gas pumped into the inlet 106 through opening 130 travels through the base and stem portions 132 of the internal channel, and through the hinge portion 134 and the halo portion 136 of the internal channel to be emitted out through gas openings 112.

Figure 4A:
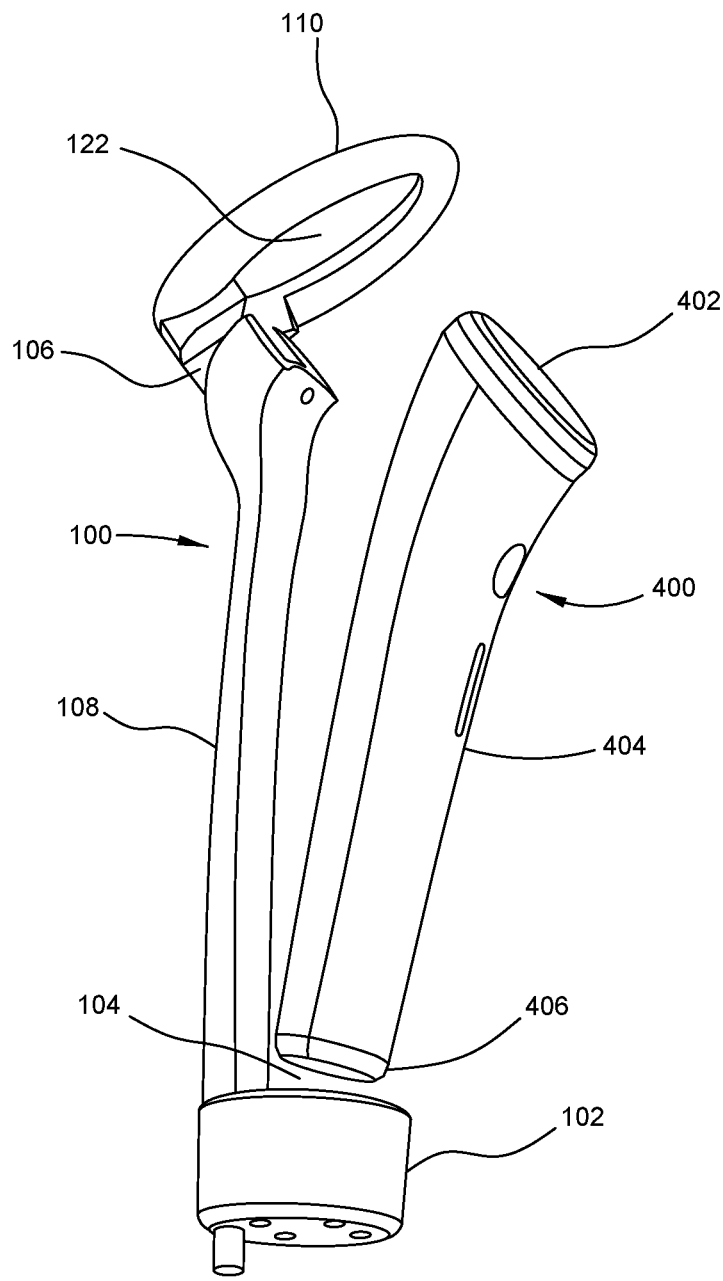
FIGS. 4A-4C show a sequence of placing a skin care device into the handle device, in accordance with some embodiments.
Figure 4B:
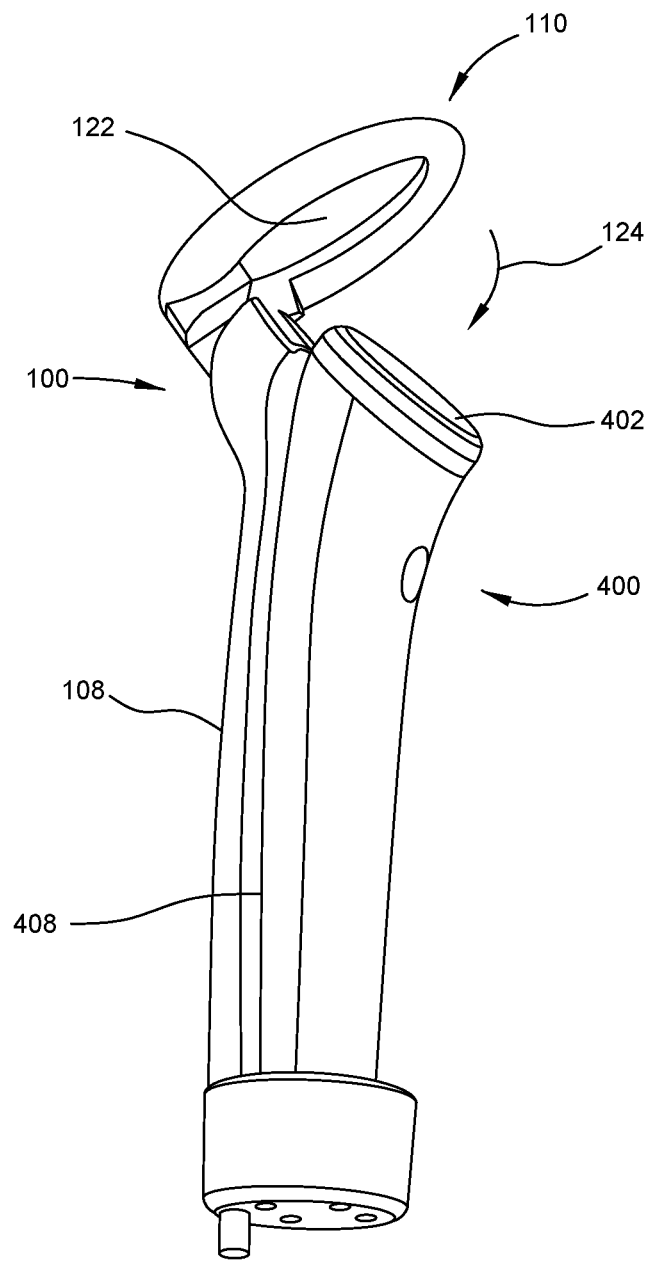
Figure 4C:
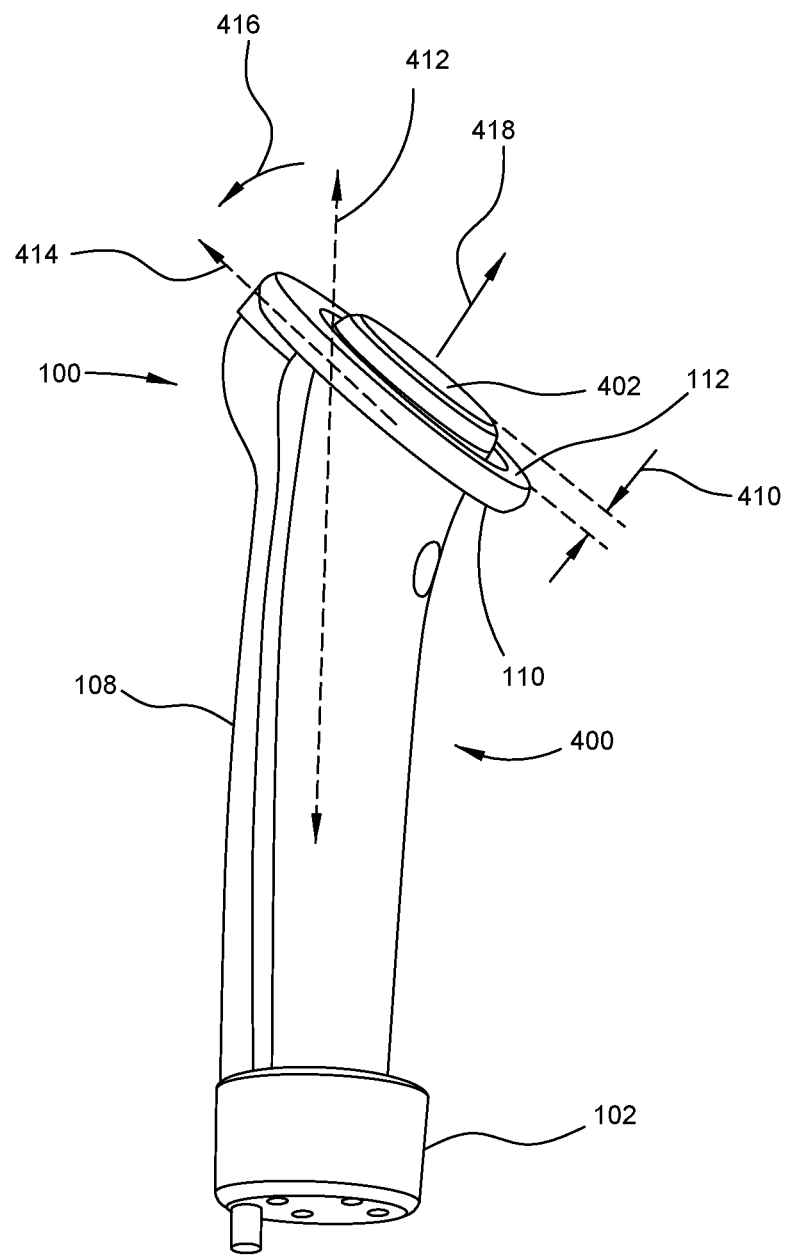

FIGS. 4A-4C show an exemplary sequence of placing a skin care device into the holder device 100, in accordance with some embodiments. The skin care device 400 shown here is an example of one form factor of such a device, and it will be understood by those skilled in the art that other shapes of such devices can likewise be accommodated in a holder device that is configured to accept those other form factors without departing from the inventive embodiments disclosed herein.

In FIG. 4A, the halo 110 is raised about the hinge 106. A skin care device 400 is then placed into the handle device 100 by placing the bottom 406 of the skin care device 400 on the top 104 of the base 102 of the handle device 100. The exemplary skin care device 400 shown here includes a generally cylindrical body 404 where the user grasps the skin care device 400 to hold it during use. At the top of the body 404, opposite the bottom 406, is a head 402 that comprises a transparent or translucent cover through which light is emitted. In other embodiments of the skin care device the head may have an opaque head/cover with light openings through which light is emitted. The head/cover 402 can be flat and planar and at about a forty five degree angle relative to an axis along the body 404, although the angle of the head depends on the design of the skin care device. The particular angle is not critical, however, and other angles, even orienting the cover to be perpendicular or parallel to the axis of the body 404 will work equivalently. The skin care device 400 can have a power button (not shown) to turn on the light elements in the head 402 to emit light, as desired. In FIG. 4B the skin care device 400 is moved from the position shown in FIG. 4A so that the back of the skin care device 400 is aligned with, if not in contact with, the stem 108 of the handle device 100. At which point the halo 110 can then be lowered as indicated by arrow 124. When the halo 110 is fully lowered, the arrangement of FIG. 4C will be achieved. In the lowered position the top 112 of the halo 110 is generally parallel to the top of the head 402 of the skin care device 400. The angle 416 of the axis 412 of the skin care device 400 and the plane 414 in which the halo 110 is positioned when closed can be, in some embodiments, in the range of thirty to sixty degrees. In other embodiments the angle 416 can be greater or smaller, depending on the design of the skin care device being held. The top of the head 402 of the skin care device 400 extends through the through opening (122) in the halo 110 by a distance 410, and is thereby encircled by the halo 110. The distance 410 can range from one tenth of an inch to about one half an inch, or about two and half millimeters to about 13 millimeters. This distance 410 is useful to ensure that the user's skin doesn't block the gas openings 114 in the top 112 of the halo 110. Aligning the top 112 of the halo 110 to be parallel to the surface of the head 402 ensures that each of the gas openings 114 will be the same distance 410 from the surface of the head 402. This helps ensure that the oxygen/gas emitted from the gas openings 114 of the halo 110 is distributed fairly equally about the head 402 of the skin care device 400. In general, the head 402 of the skin care device 400 and the top 112 (top or front surface) of the halo 110 are oriented in the same direction 418 when the halo 110 is in the lowered position for use. When the head 402 has a flat, planar front surface, then the direction 418 is perpendicular to the plane of the front surface of the head 402.

Figure 8:
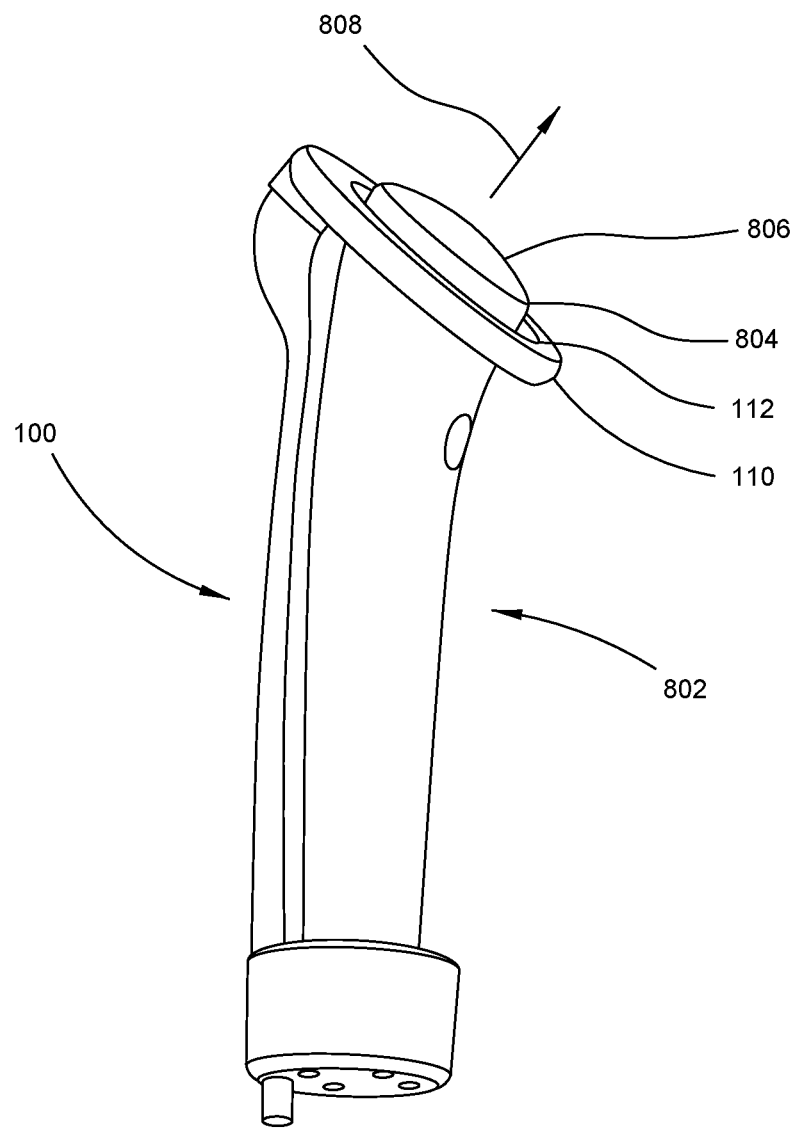
FIG. 8 shows a skin care device having a head with a convex surface used with handle device, in accordance with some embodiments.

In some embodiments, the front surface of the head 402 may be convex, or rounded outward, as shown in FIG. 8, in which a skin care device 802 is used with handle device 100, and has a head 804 having a convex front surface 806 that is facing in direction 808. Likewise, the top 112 of the halo 110 is oriented in the same direction 808. The direction 808 is generally perpendicular to a plane defined by the base or edges of the convex surface at the sides of the head 804, and is in a direction in which the skin care device is intended to be moved for optimum skin contact with the user's skin.

As shown in FIG. 4C, the handle device 100 and skin care device 400 are ready to be used together. The handle device 100 can have features for holding the skin care device 400 in place. For example, there can be a magnet located in the base 102 of the handle device 100, and/or in the stem 108 that attracts the skin care device 400. The halo 110 can be configured to bear against a portion of the skin care device, as well, such as a slight shoulder or protrusion, in some embodiments.

The handle device 100 is intended to hold the skin care device 400 with minimal ergonomic impact, while being able to provide oxygen near and around the head 402 of the skin care device 400. The head 402 of the skin care device 400 being the portion of the skin care device 400 that is intended to be applied to the user's skin, or held nearest the user's skin. Accordingly, the stem 108 of the handle device 100 extends along the back of the skin care device 400 rather than surrounding the skin care device 400, which would make the combination of the skin care device 400 and holder device 100 bulkier to grasp together. Also, the stem 108 has a thickness, in a direction perpendicular to the side of the skin care device 400, that is minimized so as to not interfere with the handling of the skin care device 400. The gas openings 114 in the top 112 of the halo 110 can be distributed around the halo 110 symmetrically to ensure coverage around the head 402 of the skin care device 400.

Figure 5:
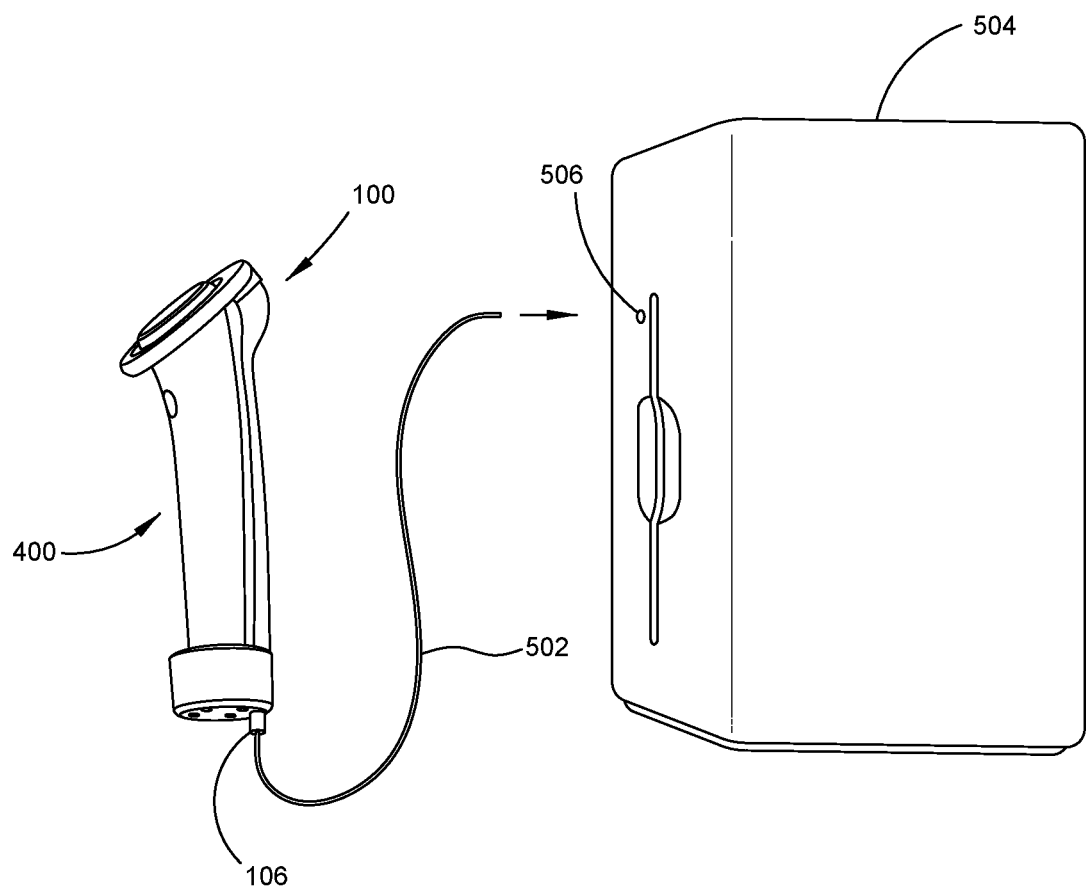
FIG. 5 shows a system including an oxygen generator and a skin care device in the handle device, in accordance with some embodiments.

FIG. 5 shows a system 500 including an oxygen generator 504 and a skin care device 400 in the handle device 100, in accordance with some embodiments. A tube 502 connects the oxygen generator 504 to the handle device 100. Specifically, the tube 502 is connected at one end to an outlet 506 of the oxygen generator 504, and to the inlet 106 of the handle device 100 at the other end of the tube 502. Upon being turned on, the oxygen generator 504 generates oxygen and pumps the oxygen through the tube 502, where it passes through the handle device 100 and out of the gas openings (114) on the top of the halo (110). The oxygen generator 504 can generate oxygen by electrolysis of water, or it can be an oxygen concentrator that excludes non-oxygen constituents from air and provides highly oxygenated air to the handle device 100.

Figure 6:
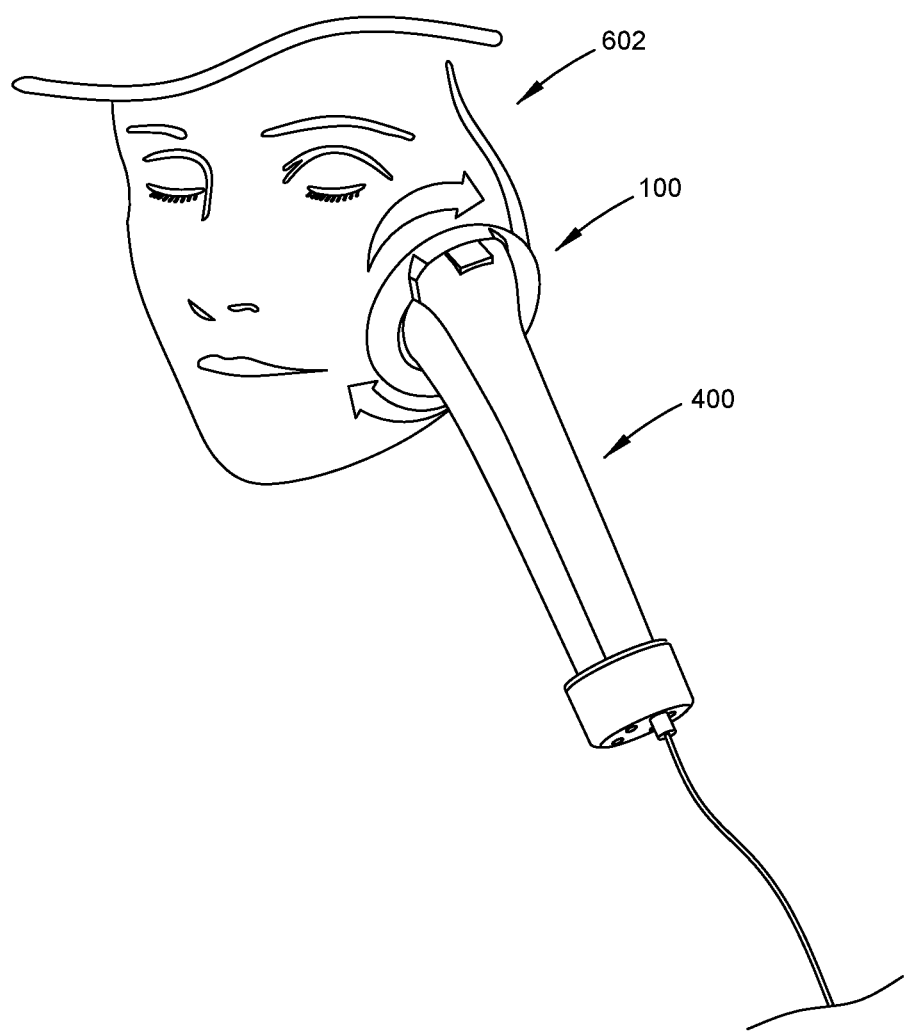
FIG. 6 shows a use of the skin care device in the handle device, in accordance with some embodiment.

FIG. 6 shows a use of the skin care device 400 in the handle device 100, in accordance with some embodiments. Both the oxygen generator 504 and the skin care device 400 are turned on. The amount of oxygen supplied by the oxygen generator and the amount and type of light output by the skin care device 400 can be selected by the user. Then the user applies the head of the skin care device 400 to their skin, such as on their face 602. Then the user can move the skin care device 400 and handle device 100 so that the face of the head of the skin care device 400 moves in a generally circular motion. This ensures that skin to which light is applied is then exposed to the oxygen being emitted by the handle device 100. The user can additionally slowly move the skin care device 400, in the handle device 100, across their face 602 while continuing to make the generally circular motion. The exposure time can be controlled or determined by the user.

Figure 7A:
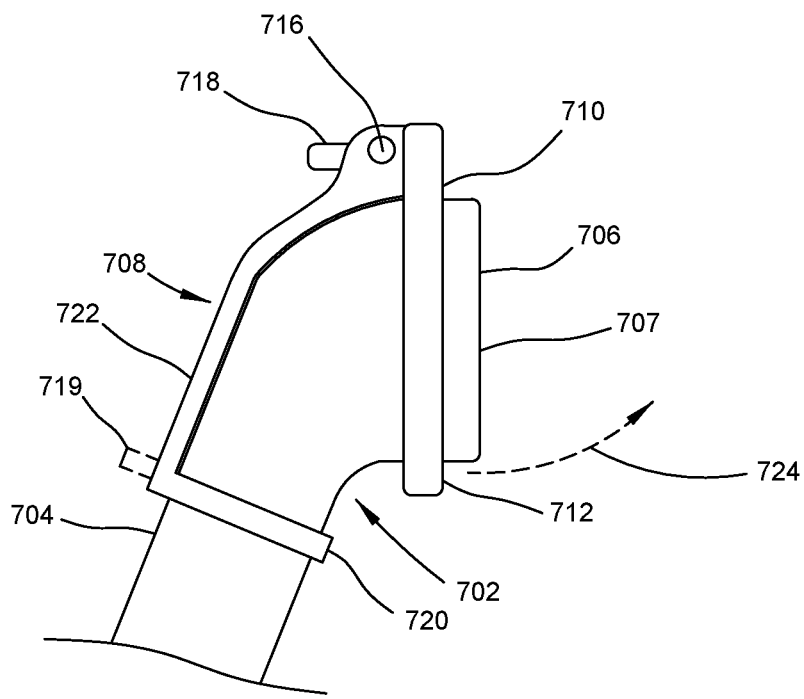
FIGS. 7A and 7B show side and front elevational views of a handle device that is configured to attach to a skin care device to provide oxygen around the head of the skin care device.
Figure 7B:
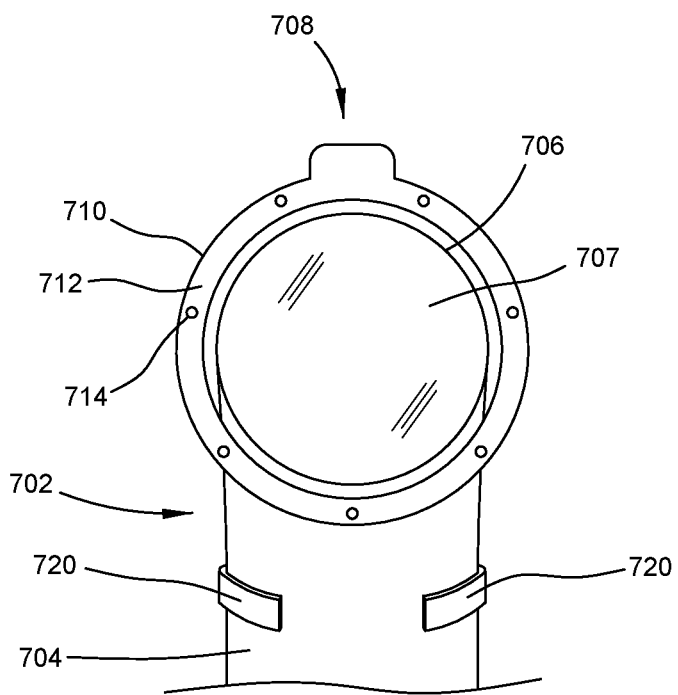

FIGS. 7A and 7B show side and front elevational views, respectively, of a handle device 708 that is configured to attach to a skin care device 702 to provide oxygen around the head 706 of the skin care device 702. In this embodiment, the handle device 708 doesn't hold the skin care device 702, rather, the handle device 708 attaches to the body 704 of the skin care device 702. The skin care device 702 has a body 704 that is elongated and substantially cylindrical and can act as a handle for the skin care device 702 where the user grasps the skin care device 702. At the top of the body 704 is a head 706. The head 706 comprises a cover member through which light can be emitted. The head can have a flat, planar outer surface 707, or the outer surface 707 can be convex in some embodiments. The outer surface 707 of the head 706 of the skin care device 702 is intended to be placed gently against the user's skin as the skin care device 702 is moved around the user's skin while emitting light from the head 706.

The handle device 708 is used to add oxygenation to the light treatment provided by the skin care device 702, and includes a halo 710 that at least partially encircles the head 706 of the skin care device 702. The halo 710 has a surface 712 that faces in the same direction as the head 706 of the skin care device 702, and gas openings 714 in the surface 712 are contiguous with a channel inside the halo 710 that is fluidly connected to an inlet 718, or 719. Inlet 718 is near the top of the handle device 708 where the halo 710 is hinged (by hinge 716). Inlet 719 may be used instead of inlet 718 in some embodiments and is located near the bottom of the stem 722 of the handle device 708. A channel through the stem connects the inlet to the channel in the halo 710. Oxygen or another gas or gasses can be pumped into inlet 718/719 and then emitted through gas openings 714 in the surface 712 of the halo 710. The stem 722 is coupled to a pair of clip members 720 that partially encircle the body 704 of the skin care device 702 to hold the handle device 708 in place on the skin care device 702. The halo 710, as mentioned, is hinged about hinge 716, and can be lifted about the hinge 716 as indicated by arrow 724 for connecting the handle device 708 to the body 704 of the skin care device 702. As shown here, it is generally preferable for the surface 712 of the halo 710 to be set back from the front surface 707 of the head so that as the user presses the head 706 against their skin, their skin will not block the openings 714. In an alternative embodiment, the halo 710 can be fixed in place rather than being hinged, and it can be placed over the head of the skin care device while the handle device is attached to the skin care device, or while the bottom of the skin care device is placed on a base of the holder device.

A handle device has been disclosed that is used to hold, or attach to, a portable, hand held skin care device in order to supplement the light therapy provided by the skin care device with oxygen, or another gas or gasses. The skin care device has a head that is intended to be placed in contact with a user's skin, and the head contains light elements that produce the light emitted at the head into the user's skin. The handle device include a halo portion that at least partially encircles the head of the skin care device such that the head of the skin care device extends through a through-opening of the halo. The halo is joined to a stem portion of the handle device, either by a hinge or in a fixed manner. There is an inlet on the handle device configured to be a gas input where gas is pumped into the handle device. The gas passes through the inlet, and through a contiguous channel through the inside of the handle device to gas openings at a front of the halo so that the gas is provided proximate to the head of the skin care device in order to provide the benefit of oxygenating the skin being treated by the skin care device.

The claims appended hereto are meant to cover all modifications and changes within the scope and spirit of the present invention.

What is claimed is:

1. A handle device for emitting a gas proximate to a head of a skin care device having a head, comprising:
    a halo that at least partially surrounds the head of the skin care device and which defines an opening through which the head of the skin care device passes and extends in front of the halo when the handle device is attached to the skin care device;
    the halo having an internal channel, and a plurality of gas openings that are fluidly coupled to the channel; and
    an inlet having a bore that is fluidly coupled to the internal channel of the halo.

2. The handle device of claim 1, wherein the halo has a front surface in which the plurality of gas openings are disposed, and which faces in a same direction as the head of the skin care device.

3. The handle device of claim 1, further comprising a stem having a top, and wherein the halo is coupled to the top of the stem.

4. The handle device of claim 3, wherein the halo is hingeably coupled to the top of the stem, and is moveable between a raised and a lowered position.

5. The handle device of claim 3, wherein the inlet is disposed on the stem, and the stem includes a channel from the inlet to the internal channel of the halo.

6. The handle device of claim 3, wherein the stem extends to a base that is configured to bear against a portion of the skin care device.

7. The handle device of claim 6 wherein the inlet is disposed on the base, and is fluidly coupled to a channel in the stem that is coupled to the internal channel in the halo.

8. The handle device of claim 3, wherein the stem has a bottom and the device further includes a pair of opposing clip members configured to extend partly around a body of the skin care device.

9. A handle device for use with a skin care device, the skin care device having a body with a head at one end of the body and a bottom at an opposite end of the body from the head, the handle device comprising:
    a base having a top that is configured to bear against the bottom of the skin care device;
    a stem that extends from the base to a top of the stem;
    a halo coupled to the top of the stem by a hinge such that the halo is moveable about the hinge between a lowered position and a raised position, the halo being configured to surround the head of the skin care device and having a through opening configured to allow the head of the skin care device to extend there through, the halo further having a top surface that has a plurality of gas openings around the top surface of the halo, the halo further comprising a channel inside the halo that is fluidly coupled to each gas opening of the plurality of gas openings; and
    an inlet having an opening, wherein there is a channel inside the handle device between the opening of the inlet and the channel inside the halo.

10. The handle device of claim 9, wherein the inlet extends from the base, and the channel extends through the stem to the halo.

11. The handle device of claim 9, wherein the stem extends from a back of the base, at the top of the base.

12. The handle device of claim 9, wherein, in the lowered position, the top surface of the halo is configured to be set back from a front surface of the head of the skin care device.

13. A handle device for use with a skin care device, the skin care device having a body with a head at one end of the body and a bottom at an opposite end of the body from the head, the handle device comprising:
   a gas emitting portion that is configured to be positioned proximate to the head of the skin care device when the handle device is used with the skin care device, the gas emitting portion having at least one gas opening; and
   an inlet, and wherein there is a channel inside the handle device between the inlet and the at least one gas opening of the gas emitting portion.

14. The handle device of claim 13, wherein the gas emitting portion is a halo that is configured to at least partially surround the head of the skin care device, the handle device further comprising:
   a base;
   a stem extending from the base, the stem having a top, wherein the halo is coupled to the top of the stem; and
   wherein the inlet is located on the base the channel extends through the stem to the halo.

15. The handle device of claim 14, wherein the halo is couple to the top of the stem at a hinge that allows the halo to be moved between a raised position and a lowered position.

16. The handle device of claim 13, further comprising:
   a stem having a top, wherein the gas emitting portion is connected to the stem at the top of the stem, and wherein the stem has a bottom from which a pair of opposing clip members extend that are configured to clip onto a body of the skin care device.

17. The handle device of claim 13, wherein the gas emitting portion is a halo that is circular and is configured to at least partially surround the head of the skin care device.

18. The handle device of claim 17, wherein the at least one gas opening is a plurality of gas openings distributed around the halo.

19. A method of providing oxygen with a skin care device, the skin care device having a head that emits light, the method comprising:
   providing a handle device having a halo which defines an opening, the handle device having an internal channel and the halo having a plurality of gas openings that are fluidly coupled to the channel, the handle device further having an inlet having a bore that is fluidly coupled to the internal channel;
   placing the skin care device into the handle device such that the head of the skin care device passes through the opening defined by the halo, and extends in front of the halo;
   connecting an oxygen source to the inlet; and
   applying the head of the skin care device to a person while also providing oxygen from the oxygen source to the handle device such that oxygen is emitted through the gas openings of the halo.

20. The method of claim 19, further comprising:
   providing the handle device with a base; and
   wherein coupling the handle device to the skin care device comprises placing a bottom of the skin care device onto a top surface of the base of the handle device.

* * * * *